United States Patent [19]

Wolf et al.

[11] Patent Number: 5,518,002
[45] Date of Patent: May 21, 1996

[54] PORTABLE ELECTRONIC SPIROMETRIC DEVICE

[75] Inventors: James L. Wolf; Daniel V. Sallis, both of Littleton, Colo.

[73] Assignee: Medtrac Technologies, Inc., Lakewood, Colo.

[21] Appl. No.: 140,752

[22] Filed: Oct. 22, 1993

[51] Int. Cl.[6] ........................... A61B 5/087; A61B 5/091
[52] U.S. Cl. ............................................. 128/725; 482/13
[58] Field of Search .................................... 128/716, 724, 128/725, 719, 671; 482/13

[56] References Cited

U.S. PATENT DOCUMENTS

| | | | |
|---|---|---|---|
| 3,577,984 | 5/1971 | Levy et al. | 128/725 |
| 3,645,133 | 2/1972 | Simeth et al. | 128/725 |
| 3,687,130 | 8/1972 | McCormick | 128/724 |
| 3,913,379 | 10/1975 | Rusz et al. | 128/719 |
| 3,962,917 | 6/1976 | Terada | 128/725 |
| 4,036,217 | 7/1977 | Ito et al. | 128/724 |
| 4,158,360 | 6/1979 | Adams | 128/725 |
| 4,640,293 | 2/1987 | Garbe | 128/725 |
| 4,830,022 | 5/1989 | Harshe et al. | 128/724 |
| 5,094,246 | 3/1992 | Rusz et al. | 128/724 |
| 5,224,487 | 7/1993 | Bellofatto et al. | 128/725 |
| 5,277,195 | 1/1994 | Williams | 128/725 |
| 5,279,304 | 1/1994 | Einhorn et al. | 128/724 |

*Primary Examiner*—Lee S. Cohen
*Assistant Examiner*—Brian M. Green
*Attorney, Agent, or Firm*—Edwin H. Crabtree; Donald W. Mangolis

[57] ABSTRACT

A portable hand held electronic spirometric device for analyzing the strength of the exhalation of a patient under a doctor's care. The electronic spirometric device is designed to sense and measure exhaled air flow rate and exhaled breath temperature, determine air flow volume, and record and display the respiratory movement of the patient for helping make medication recommendations. The spirometric device includes an electronic package mounted inside a hand held housing for computing and recording the strength, the temperature, and the volume of the exhalation along with the time and date of the exhalation. The device includes a replaceable air flow chamber mounted on the housing. A disposable mouthpiece is releasably attached to the air flow chamber. A hot wire acting as an anemometer is disposed inside the air flow chamber and provides for measuring both air flow rate and temperature. An output of the hot wire is connected to electronic circuitry inside the housing for determining the proper proportion and evaluation of the peak flow rates and volumes along with recording the exact time and date of the measured event. The device is also designed to give interpretive feedback and recommendations which are pre-programmed by the doctor for the patient and to detect before hand a possible chronic episode, for example a pending asthmatic attack, and alert the patient to take necessary medication to avert the episode. The portable device may be periodically connected to a computer system to up-load stored information and provide a chronological report stored therein for analysis by the doctor. The stored data can be transferred from the spirometric device via telephone and modem to the doctor's office.

17 Claims, 11 Drawing Sheets

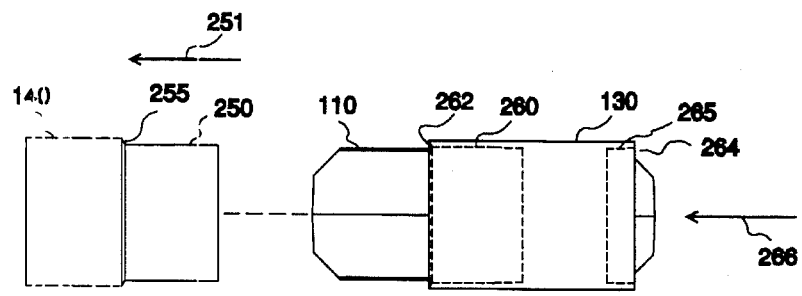
FIGURE 2c
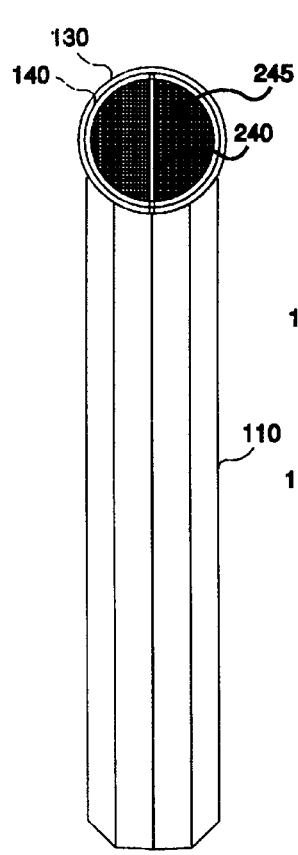
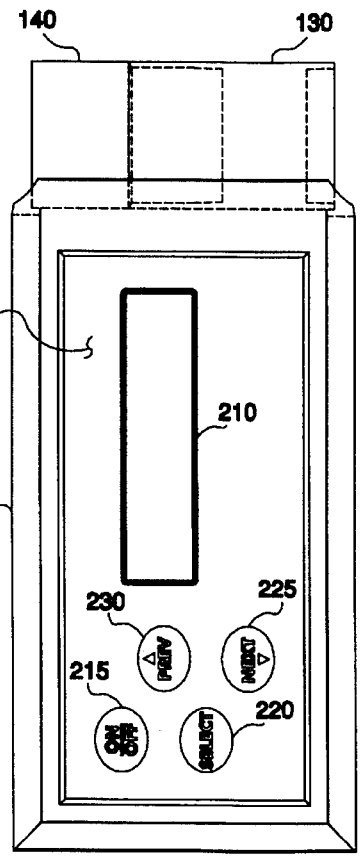
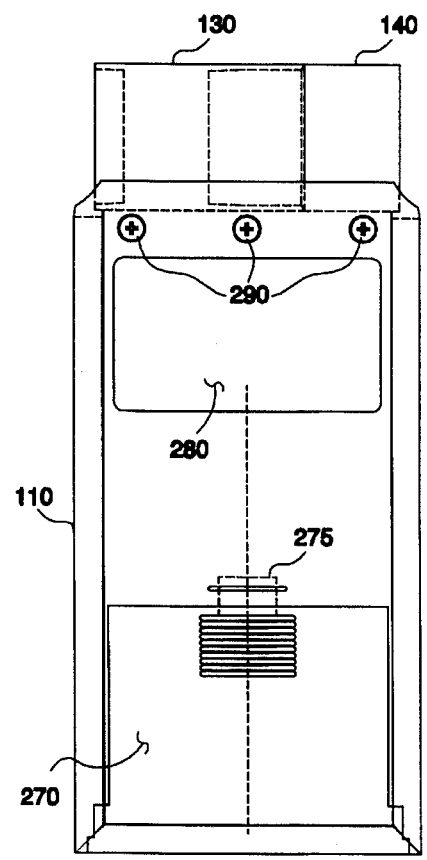
FIGURE 2b　　　　FIGURE 2a　　　　FIGURE 2d

"A"

"B"

"C"

"D"

"E"

PORTABLE ELECTRONIC SPIROMETRIC DEVICE

BACKGROUND OF THE INVENTION

1. Related Inventions

The present invention is related to the following co-pending applications, Medication Inhalant Device, filed on Sep. 16, 1993 and having a Ser. No. 08/122128 and Dry Powder Inhalant Device, filed on Sep. 16, 1993 and having Ser. No. 08/122126.

2. Field of the Invention

This invention pertains to a device and a system for the measurement and display of the volume and flow rate of exhaled air from a person. The small pocket sized electronic spirometer known as the Peaklog measures and records the respiratory measurements and can additionally give interpretive feedback and recommendations pre-programmed by a physician. The activity is recorded in non-volatile memory which may be retrieved by a personal computer and graphically displayed and analyzed in a chronologic report.

3. Discussion of Prior Art

Prior to the filing of this application, the inventor conducted a patentability investigation for a system that monitors breathing, and provide a chronlogical report for all activity therewith. The following patents were uncovered in the search:

| Inventor | Reg. No. | Date |
| --- | --- | --- |
| Boehringer | 3,871,364 | Mar 18, 1975 |
| Monroe | 3,949,737 | Apr 13, 1976 |
| Edwards, Jr. et al. | 4,421,120 | Dec 20, 1983 |
| Tamm | 4,679,566 | Jul 14 1987 |
| Varraux et al. | 4,768,520 | Sep 6, 1988 |
| Rusz et al. | 5,094,246 | Mar 10, 1992 |
| Wood et al. | 5,097,429 | Mar 17 1992 |
| Waterson et al. | 5,137,026 | Aug 11, 1992 |
| Kerr et al. | 5,200,891 | April 6,1993 |

Discussion of Discovered Prior Art

The patent issued to Boehringer (U.S. Pat. No. 3,871,364) describes a mechanical peak expiratory flow device (PFER) with a spring loaded piston and a peak reading indicator.

The patent issued to Monroe (U.S. Pat. No. 3,949,738) also describes a mechanical PFER device with a series of openings which indicate the peak expiratory flow. The patent issued to Edwards, Jr. et al. (U.S. Pat. No. 4,421,120) describes a PFER device which has an audible indicator (reed) which will indicate that flow has exceeded a threshold.

The patent issued to Tamm (U.S. Pat. No. 4,679,566) describes an apparatus for measuring several physiological parameters, namely, pulse rate, forced vital capacity and pulmonary peak flow (PFER). The pulmonary measurement part utilizes a turbine flow meter to make flow measurements. Simple counting circuits can display the peak flow rate and volume (vital capacity).

The patent issued to Varraux et al. (U.S. Pat. No. 4,768, 520) describes a mechanical PFER device with incentive meter which can also be used for inspiration. It has a magnetic slider which will maintain the peak reading.

The patent issued to Rusz et al. (U.S. Pat. No. 5,094,246) describes an electronic hot wire anemometer for pulmonary gas flow measurements. Its primary focus is on a quick calibration mechanism built in the flow sensor.

In the 1992 patent issued to Wood et al. (U.S. Pat. No. 5,097,429) pertains to a user programmable microprocessor based apparatus which acts as a reminder to a medication schedule of events. When user programs parameters relating to intervals of medication, the device prompts the user by signaling alarm.

The patent issued to Waterson et al. (U.S. Pat. No. 5,137,026) describes an electronic personal portable spirometer capable of making the standard respiratory measurements of forced expiratory volume (FVC) and peak expiratory flow (PFER and FEV1). These measurements are displayed on a screen on the housing of the device. The flow measurement sensor is based on differential pressure across a nonlinear flow resistor. A microprocessor linerizes the output from this sensor to be displayed. The device contains a keyboard to operate the unit.

The patent issued to Kehr et al (U.S. Pat. No. 5,200,891) pertains to a device having a plurality of compartments, each of which store medication pills and an electrical signaling system to emit medication alert signals. The disclosed signals indicate that medication should be taken, from which compartment and the quantity. The device of Kehr has a high degree of inter-action between the user and its operation by selecting push-buttons and reading messages on the device display.

None of the above approaches discloses an approach for a portable electronic spirometric device utilizing hot wire anemometer technology, for chronologically recording and displaying the spirographic detail of the user, and make interpretive recommendations as were pre-programed.

SUMMARY OF THE INVENTION

The present invention sets forth a portable, highly miniaturized device which, precisionly measures peak expiratory flow rates and volumes, and chronologically records all activity. The device can make recommendation, based on performance, to take medication and quantify the results, and further remind the patient to use the device at predetermine times. The device includes sensors placed in the approximate path of the user's exhalation mounted in a easily replaceable air flow chamber and a disposable mouthpiece. The output of the sensors is delivered into sophisticated circuitry for determining the proper proportion and evaluation of peak flow rates and volumes, and makes a record of the event including the exact time and date. The determining circuit is capable of giving warning to the patient that something less then proper flows and volumes has been detected, and to act accordingly. The principle is to detect before hand a possible chronic episode, for example in a pending asthmatic attack, and to take the correct amount of medication to alleviate said attack before becoming critical.

The subject chronolog apparatus is periodically connected to a system to up-load stored information and analyze the chronologic report stored within. This may be accomplish directly or through telephone and modem to a physician's office.

Most present spirometer devices determine the flow by measuring the pressure drop across a resistance to flow in the air passage. To make this measurement predictable, the flow through the resistor is maintained in a laminer state. This has the additional advantage of providing essentially a linear pressure drop versus volumetric flow. Thus, a simple differential pressure measurement provides an output signal which is approximately proportioned to the volumetric flow.

The disadvantage of those types of instruments is that to keep the flow in the laminar range the flow resistance tube becomes bulky and the pressure drop significantly large. Conversely with the hot wire flow measuring approach the size of the flow detector can be made considerably smaller and the pressure drop is much less. The disadvantage of the hot wire approach is that it puts out a non-linear signal, measures mass flow rather than the desired volumetric flow and the wire requires power to heat it along with a fairly complex circuit to control it.

The present invention takes the advantage of the much smaller size capability of the hot wire sensor to provide a significantly smaller, pocket size, spirometer. The above mentioned disadvantages are overcome through the use of a microprocessor driven control and recording circuit as described in the following detailed description. Further advantages of the present invention are that the hot wire flow sensor is easier to keep clean and more practical to replace as necessary to maintain a medically clean and, if necessary, even a sterile air flow passage. The hot wire can be heated to burn off contaminants, similar to a self cleaning oven, is more open for a washing process and can be made as a plug-in module for simple replacement. Conversely, the laminar flow tube resistance type sensor uses an array of very small tubes which are costly to manufacture and more susceptible to contamination and difficult to clean. A further advantage of the present invention hot wire design is that there are no air passage ways leading from the flow tube into other parts of the device. Thus any contamination from a patients breath is limited to the flow sensor tube and mouth piece and both of these are plug-in replaceables. Conversely, pressure drop type flow sensors necessarily have open flow passage ways to pressure sensors which are normally not easily replaceable. In that case, replacing the flow sensor tube does not necessarily remove all previous breath contamination.

These and other objects of the present invention will become apparent to those skilled in the art from the following detailed description, showing the contemplated novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 2a is a front planar view of the device of the present invention with disposable mouthpiece stowed in its storage place, and showing display and its operating pushbuttons.

FIG. 2b is a side planar view of the device of the present invention showing air flow chamber and sensor mounting.

FIG. 2c is a rear planar view of the device of the present invention showing battery and communication access cover.

FIG. 2d is a top planar view of the device of the present invention with disposable mouthpiece detached from storage placement.

FIG. 4 is a front planar view of the electronics sensing elements of the replaceable air flow sensor assembly of FIG. 3a.

DESCRIPTION OF THE PREFERRED EMBODIMENT

Figure 1:
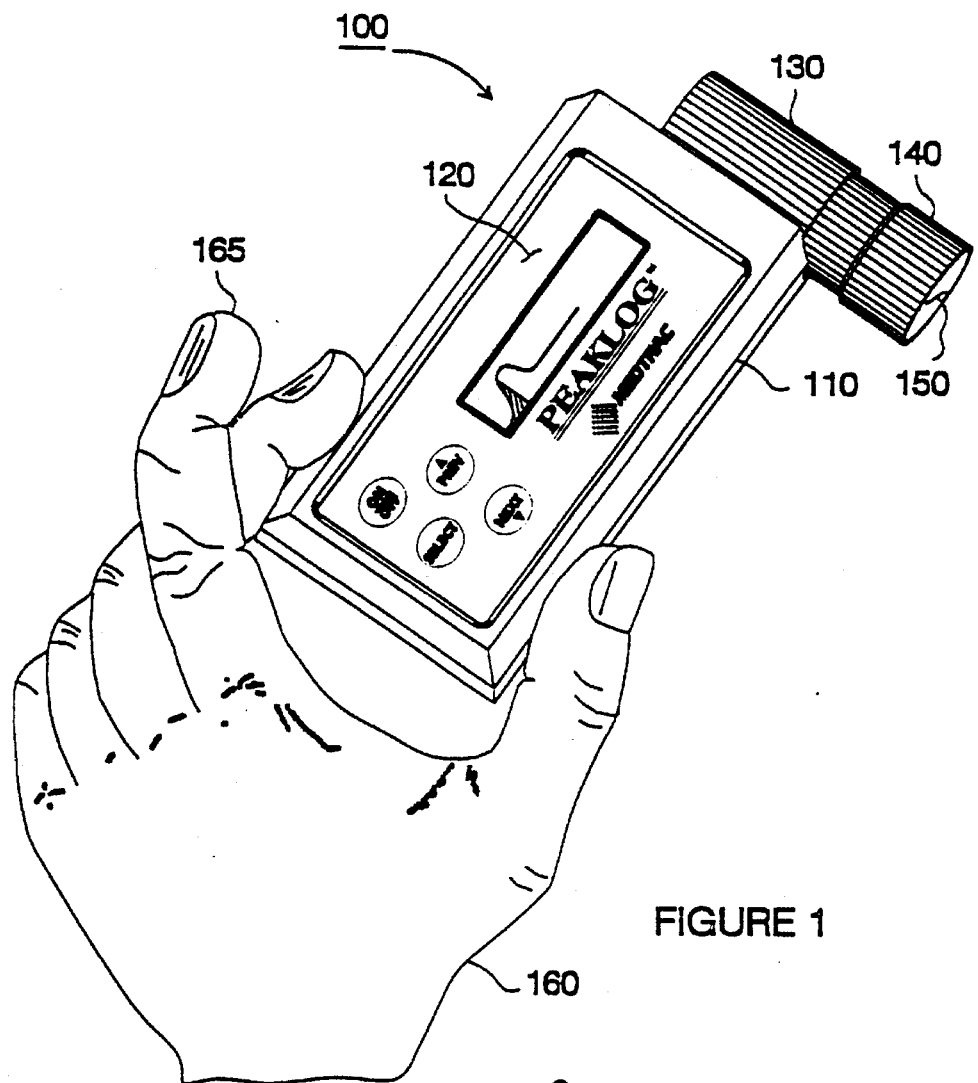
FIG. 1 sets forth a perspective view of present invention illustrated in a patient's hand as the apparatus would be used.

In FIG. 1 is shown a miniaturized, and highly portable electronic chronolog apparatus 100 of the present invention suitable for precisionly measuring peak expiratory flow rates and volumes. The apparatus 100, which is only slightly bigger then a deck of playing cards is intended to be carried on the person of patients, for example suffering from asthma, and fit handlely into a pocket or purse. The housing 110 has a control/display panel 120 on its face and has disposed on the top, a replaceable air flow chamber 130 and disposable mouthpiece 140. Mouthpiece 140 is shown in FIG. 1 as it is installed in the air flow chamber 130 during usage by a patient, with air inlet 150 easily accessible, and shall be more detailed later. It should be noted that the subject apparatus 100 is designed and constructed to comply with conventional standards as determined by the American Thoracic Society and its Standardization of Spirometry.

The apparatus 100 is illustrated in a patient's hand 160 with easy viewing of information displayed on the control/display 120. FIG. 1 further illustrates, the single hand control of operating selections with, for example, index finger 165. It is an important feature of the present invention that high precision of measured data and recording be in a convenient "personal" package intended to be as mobile as the user is able to be.

Figure 1A:
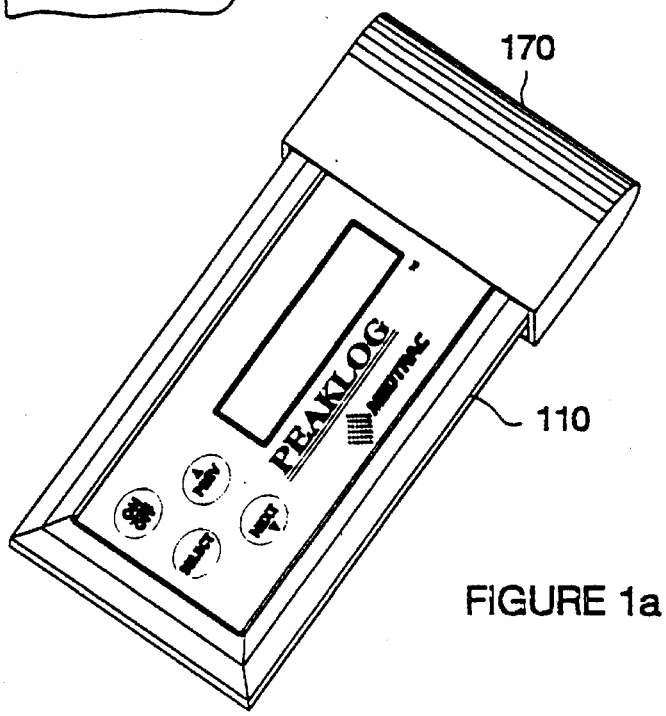
FIG. 1a is a perspective view of the present invention shown with protective cover.

In FIG. 1a the chronolog apparatus 100 is shown with its air flow protective cover 170 in place. The cover 170 is normally placed over the air flow chamber 130 and mouthpiece 140 when the unit is not in use. But more significantly, the apparatus performs a "zero" air flow calibration prior to use by the patient with the protective cover 170 in place. It is obvious that the protective cover restricts any ambient air from entering into the air flow chamber which may effect the sensors during the zero air flow calibration phase. The zero air flow calibration may be activated by the selection pushbuttons on the control/display panel 120 or an automatic function as part of the usage routine. This shall be discussed further later in the operations section of this patent disclosure.

In FIG. 2a, the control/display panel 120 is sectioned in two parts. The display section 210 showing a 16 character two line liquid crystal (LCD) component capable of activating individual pixcels allowing graphic representations (to be discussed later), and the control section, in the preferred embodiment, has an ON/OFF 215 push-button to activate the instrument. Two menu selection push-buttons, NEXT 225 and PREV 230 (previous) provide quick access to system functions. Typical menu selections are: "DO MANEUVER", "DISPLAY DATA", "DISPLAY ALARM", "DISPLAY CLOCK", "MAINTENANCE".

The SELECT 220 push-button activates the system function currently in displayed 210. The overlay control/display panel is suitable for art work layouts indicating the product name and nomenclature of each push-button.

The air flow chamber 130 is shown with disposable mouthpiece 140 in its proper stowed placement, when the device is not being used. The apparatus 100 would be place in a short pocket, purse and/or special carrying case (not shown).

In FIG. 2b, a side planar view reveals a sensor array 240, and a fine mesh screen 245 which shall be discussed later. In this view, the air flow chamber 130 and mouthpiece 140, has an unobstructive path for air to pass through the instrument except for the sensor array 240 and the fine mesh screen 245. In FIG. 2c the top planar view shows the disposable mouthpiece 140 being detached from its stowed position within air flow chamber 130. When mouthpiece 140 is stowed away, surface 250 slides into receptive inner space 260 of air flow chamber 130 until relief 255 of mouthpiece abuts the air flow chamber 130 at back end 262. The fit of surface 250 and inner space 260 are such as to hold the mouthpiece without falling out, and is cradled atop housing 110 in niche 380 (when fully assembled). When the apparatus is in use, the disposable mouthpiece is removed from its stowed cradle by pulling mouthpiece in the direction of arrow 251. It is then installed into receptive space 265 at front end 264 in the direction of arrow 266, so as surface 250 is partially engaging the space 265. Again the fit is tight enough such to maintain the mouthpiece from falling out.

The fine mesh screen 245 of FIG. 2b, is located within disposable mouthpiece 140 at the relief junction 255. The purpose of the fine mesh screen 245 is to catch any particles, such as mucus or food debris, which may be expelled when user is exhaling into the apparatus. The mouthpiece 140 may be exchanged with a new one at any time said screen becomes too contaminated or may be washed when necessary. It is obvious that if apparatus 100 is reassigned to a new patient, the inexpensive disposable mouthpiece 140 would be changed out with a new one for sanitation purposes. The air flow chamber 130 merely plugs into the housing 110 and can easily be replaced if necessary to provide a new sterile air passageway.

In FIG. 2d is shown a rear planar view, where the apparatus 100 has a battery access cover 270 and is held in place by cover latch 275. The access to the system under the cover shall be further discussed later. There is a recessed section 280 of the rear of housing 110 which provides space for an informational label (not shown), indicating simple operational instructions and a manufacturers model and unit serial number. The screws 290 hold the apparatus 100 together, and shall be discussed in more detail later.

Figures 3A, 3B:
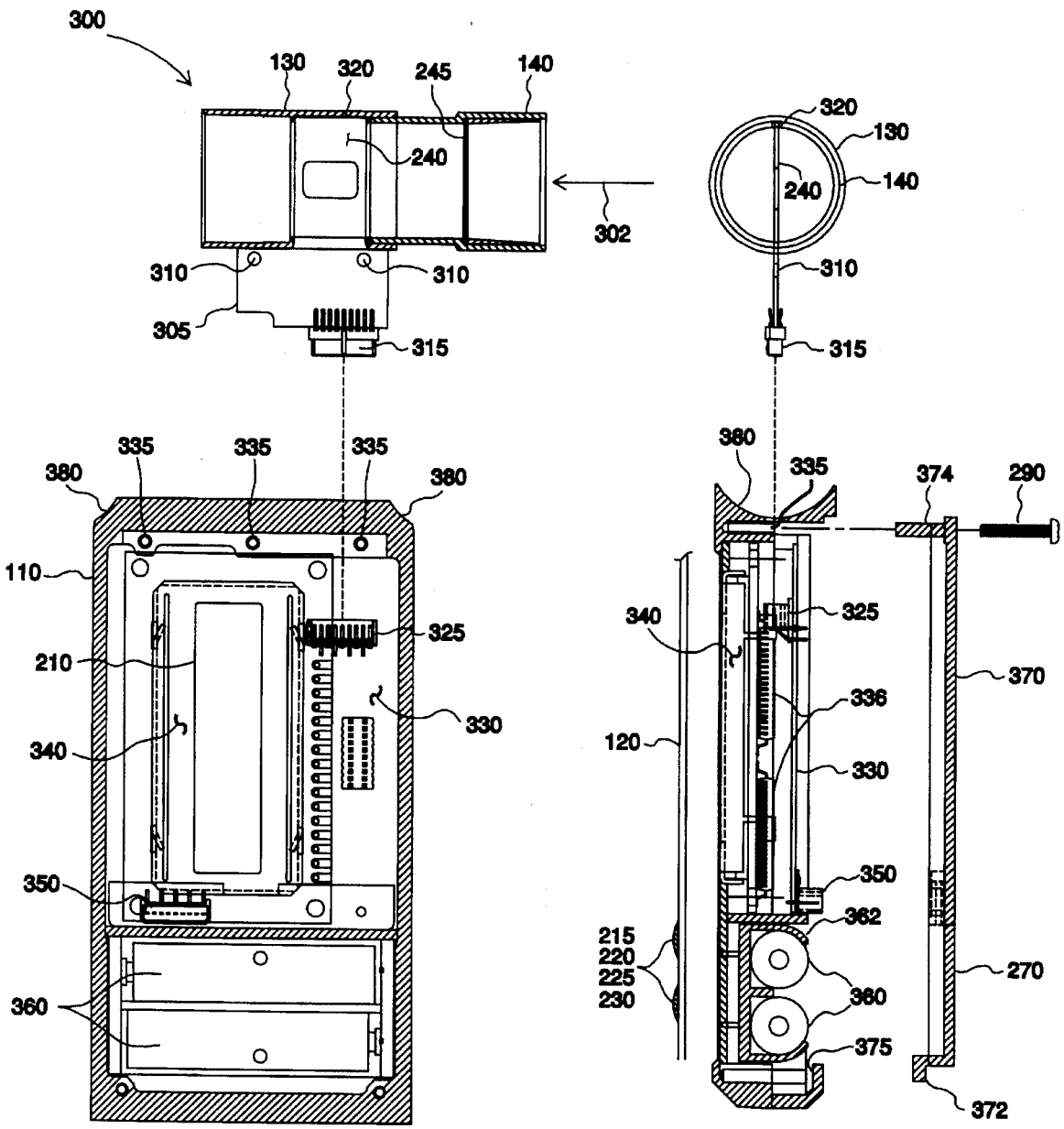
FIG. 3a is a frontal cross-sectional view showing the components within the present invention with the replaceable air flow sensor assembly detached.
FIG. 3b is a side cross-sectional view of FIG. 3a with cover and panel exploded.

In FIG. 3a is a frontal cross-sectional view showing the components within the present invention with the replaceable air flow sensor assembly 300 detached from the housing 110. Disposable mouthpiece 140 is shown installed properly in air flow chamber 130 as unit would be during use so as to show the relationship between screen 245 and sensor array 240. The air flow is indicated by arrow 302 as would be when the user exhales into the mouthpiece 140 as was earlier discussed. Screen 245 would catch any material in the air stream prior to coming in contact with sensor array 240 and exiting out back end 262 of air flow chamber 130. The sensor array is the top portion of a printed circuit board (PCB) 305 and shall be discussed in detail in FIG. 4. Mounting holes 310 and air flow sensor assembly electrical connector 315 are also located on the PCB 305. The assembly of these components comprise the replaceable air flow sensor assembly 300. This is accomplished by the air flow chamber 130 being slip over the PCB 305 top section in a slot (not shown) so as the top section (sensor array 240) engages a receptive recess 320 in the air flow 130 body inner top surface. The side view of assembly 300 is clearly shown in FIG. 3b.

Figure 5:
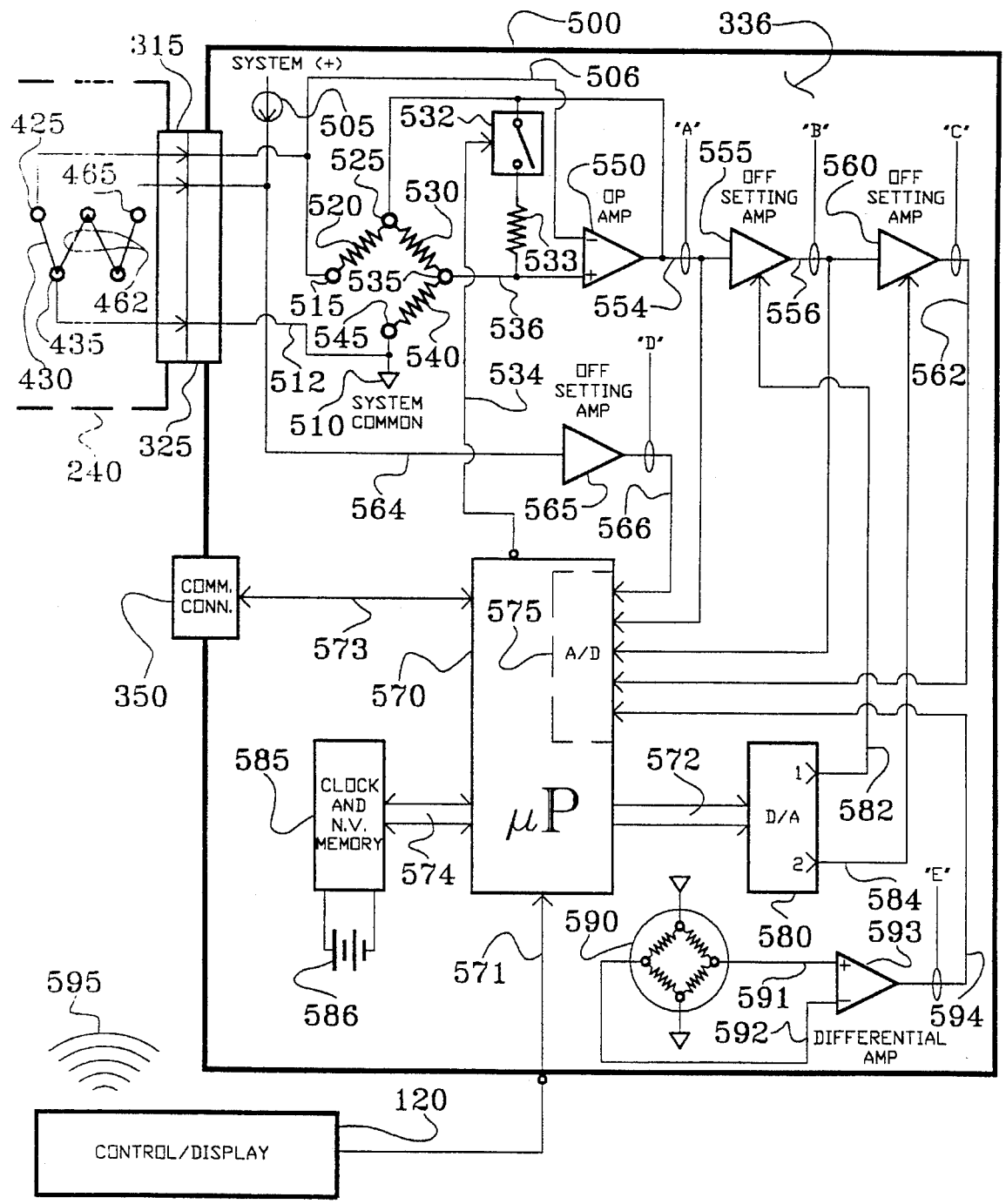
FIG. 5, 5a is a schematic block diagram of the electronics of the present invention.

Within the housing 110, is the electronics assembly 330, liquid crystal display (LCD) module 340 and batteries 360. The electronics assembly comprises a printed circuit board and the usual components including microprocessor, memory, electronic switches, etc., collectively indicated as 336, The more significant components 336 shall be discussed later in FIG. 5 as they relate to the sensing elements of the present invention. The LCD module 340, with its display 210, is electrically connected to the electronics assembly 330 (not shown). The sensor assembly connector 325 and communication connector 350 are also mounted on the electronics assembly 330 and shall be discussed later.

In FIG. 3b, is a side cross-sectional view of FIG. 3a with rear panel 370 and control/display panel 120 exploded. The layer electronics is shown in their relationship with one another. The control/display panel 120, with the selection push-buttons 215, 220, 225 and 230 are integral to an overlay which allows the LCD display 210 of the LCD module to be seen through a clear section thereon. The electrical wires of selection switches are not shown. Properly assembled, the replaceable air flow sensor assembly 300 is attached to housing 110 by first matting electrical connector 315 to receptive sensor assembly connector 325 on electronics assembly 330. Then, rear panel 370 is set in place by engaging hooked structure 372 into receptive channel 375 in housing 110 along the bottom edge. The two of three boss protrusions 374 are places through mounting holes 310 securing the replaceable air flow sensor assembly 300 firmly in niche 380 of housing 110. Finally, three screws 290 extend through the boss protrusions 374 and mat with threaded receptive holes 335. The battery access cover 270 is shown covering over the batteries 360 and external communications connector 350. If the cover is removed, it is seen that batteries may be easily accessible for replacement in their holder 362.

All of the housings and components; 110, 130, 140, 270, 275 and 370 listed thus far are plastic forms which are easily manufactured by any one skilled in the art of die and mold making. The selection push-button overlay control/display panel 120 (including art layout), PCB 310, LCD module 340, electrical connectors 325 and 350, as is components on assembly 330 comprising circuitry 336 are all conventional and may be commonly found at many electronic supply providers. The batteries 360 are conventional replaceable AA size batteries which may be commonly found in almost any store or electrical supplier.

Figure 4A:
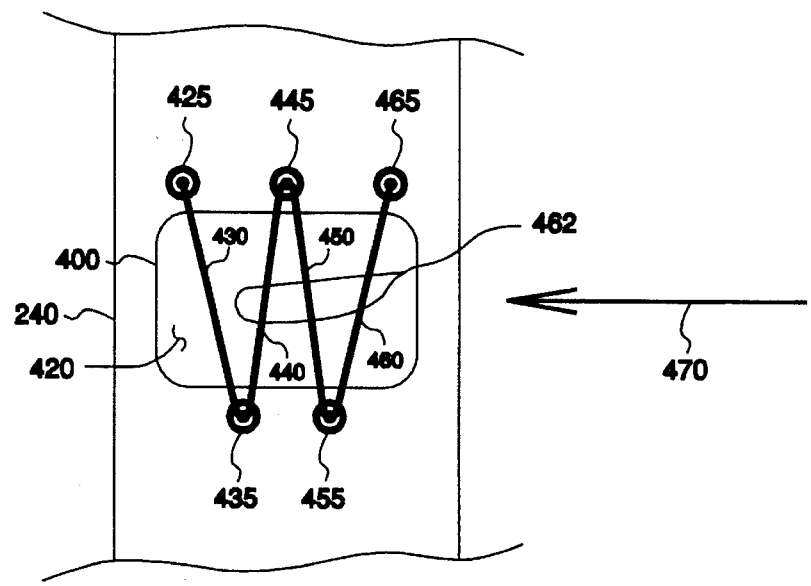
FIG. 4a is a detail view of FIG. 4 showing each of the sensing elements in their mounting.
Figure 4:
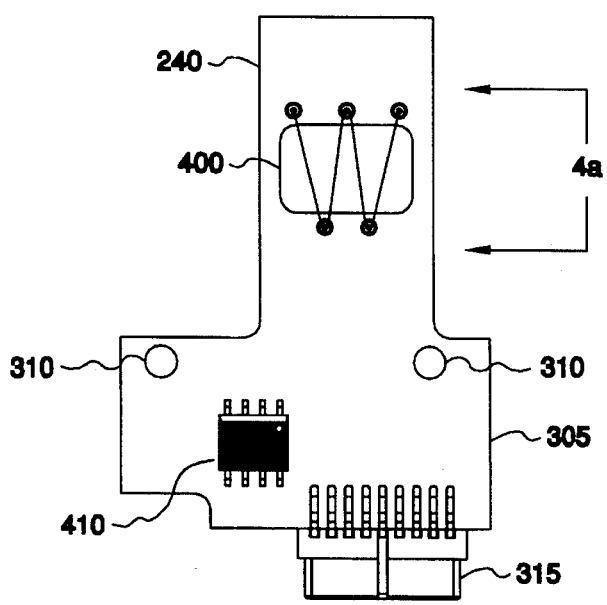

In FIG. 4, is shown the printed circuit board comprising the top portion, sensor array 240 and the bottom portion 305 as was discussed earlier. Within the top portion sensor array 240 is a rectangular hole 400 in the printed circuit board. The details of rectangular hole 400 is shown in FIG. 4a where one end of sensor element 430 is first affixed to pad 425.

Figure 4B:
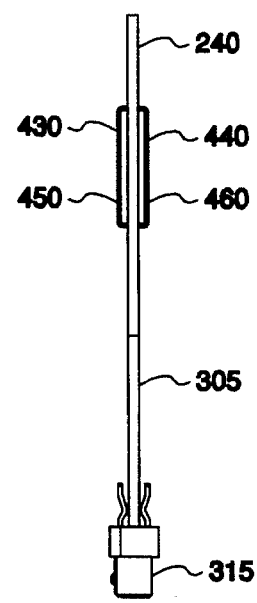
FIG. 4b is a side planar view of FIG. 4 as it is oriented in positioned during exhalation path.

Being one continuous wire, the other end is "weaved" through each of the other mounting pads 435, 445, 455 and ends at pad 465. Any slack in the wire is drawn out and each of the pads are bonded electrically with solder. Although the wire is installed as one continuous element, electrically within the circuitry the pads are connected so as to, create two main sensing elements. The "hot" sensing element 430, is connected between pads 425 and 435. The "cool" sensing element 440, 450 and 460 is connected between 435 and 465 (collectively referred to as 462), with pads 445 and 455 simply utilized as supports for the wire. The wire comprising the two main sensing elements "hot" 430 and "cool" 440, 450 and 460 is a platinum wire, 0.0007 of an inch in diameter. The wire is suspended between the pads in open space 420 and over the rectangular hole 400 as shown in FIG. 4 and 4a. The elements are shown as they would be on each side of the printed circuit board respectively because of the weaving process described above. In reality, the 0.0007 inch diameter wire would be barely discernable with out visual magnification. Further, it is to be expressly understood that any mounting scheme of the sensor elements, for example horizontally mounted from side to side in the exhalation path within air flow chamber 130, could be used instead of the weave pattern described above and that the approach shown in FIG. 4a and 4b is exemplary of one approach.

FIG. 4 further shows an electrically alterable read only memory circuit chip 410. Memory chip 410 stores the calibration and operating information about the sensing element 430 and 462 on the sensor array assembly 240. This information may be programed into the chip at time of manufacturing, and when from time to time the assembly is replaced with a new part, such information as may be relative to each individual sensor array assembly 240 is accompanied with the assembly. Also short-term memory storage of sensor calibration data may be stored into the memory chip 410. Further discussion of this feature is disclosed later.

Figure 5A:
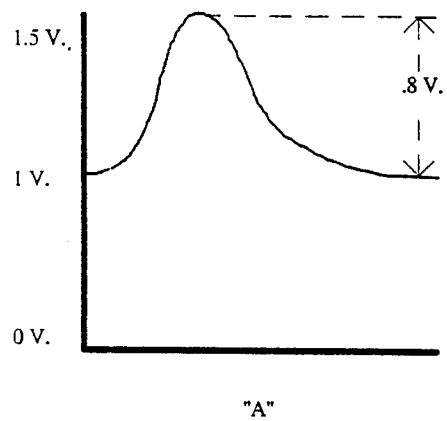

In FIG. 5a is disclosed a schematic block diagram of the electronic circuitry 336 on printed circuit board 500 of the electronic assembly 330. The system batteries 360 of FIG. 3 supply necessary voltage to energize the system through regulators and appropriate circuitry not shown on this simplified FIG. 5a. Any one skilled in the art could provide appropriate operating voltages to function the circuitry set forth in the proceeding paragraphs.

Pad 425 of the sensor array 240 is connected through connector 325 and 315 to junction 515 and the minus (−) input of operational amplifier 550 over common line 506. The system common potential 510 is connected to pad 435 of the sensor array 240 through connector 325 and 315, and further to junction 545 over common line 512. Junction 535 is connected to operational amplifier 550 plus (+) input over line 536. The output of the operational amplifier 550 is connected to junction 525 over line 552. Fixed resister 520 is connected between junctions 515 and 525. Likewise, fixed resisters 530 and 540 are connected between junctions 525 and 535, and junctions 535 and 545 respectively. Components 520, 530 and 540 along with sensor 430 compose a resistive bridge, which in operation, must be balanced. The bridge in conjunction with operational amplifier 550 form a servo loop. In operation, the servo loop functions to keep a balance between the fixed resisters 530 and 540, and fixed resister 530 and the "heated" sensing element 430. Since the only variable in the servo loop is the "heated" sensing element 430 (being that resistors 520, 530 and 540 are all fixed), The servo loop serves to supply energy to the bridge of which the sensing element 430 being of limited mass will self heat until its resistance increases to balance the bridge. Because of the fixed relationship between resistance and temperature of sensor 430 the servo loop serves to maintain a constant temperature of sensor 430 regardless of environment.

As the user would exhale into the apparatus 100, the "heated" sensing element would experience a cooling as the user's breath flows over the sensor array 240. The "heated" sensing element would change its resistance due to this cooling and the resultant imbalance causes the operational amplifier to increase its output to provide additional energy to maintain the resistance and temperature of sensing element 430. As the "heated" sensing element 430 strives to normalize (as the flow of the user's breath would diminish), the resistance of 430 increases and so the output of operational amplifier 550 decrease. An example of this servo loop operation is shown in waveform "A" of FIG. 5b as a typical exhalation. The voltage output of amplifier 550 is approximately proportional to air flow across sensor 430 to the ¼ power.

The output of operational amplifier 550 is further connected to the input of the first off-setting amplifier 555 and to the analog to digital (A/D) converter 575 of the microprocessor 570 over common line 554. The output of the first amplifier 555 is connected to the second off-setting amplifier 560 and (A/D) converter 575 of microprocessor 570 over common line 556. The output of the second off-setting amplifier 560 is connected to the A/D converter 575 over line 562. Microprocessor 570 has an address/data bus connected to digital to analog (D/A) converters 580 over line 572, and to clock and non volatile (N.V.) memory circuitry 585 over line 574. The clock an N.V. memory circuitry 585 has its own back up battery 486 power source to protect the data and information stored within should the main system batteries 360 be low in energy or are removed for replacement. The first converter of D/A converters 580 is connected to the first off-setting amplifier 555 control input over line 582, and likewise the second converter of D/A converters 580 is connected to the second off-setting amplifier 560 control input over line 584.

Figure 5B:
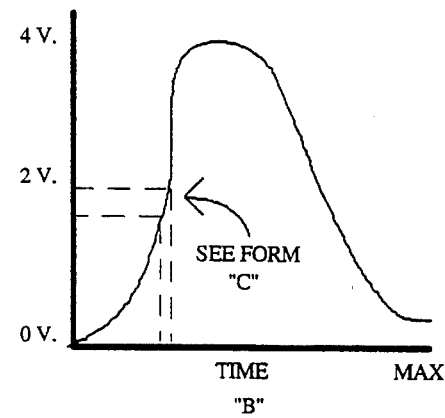
FIG. 5b–5e illustrates signal wave forms "A", "B", "C", "D", and "E".
Figure 5C:
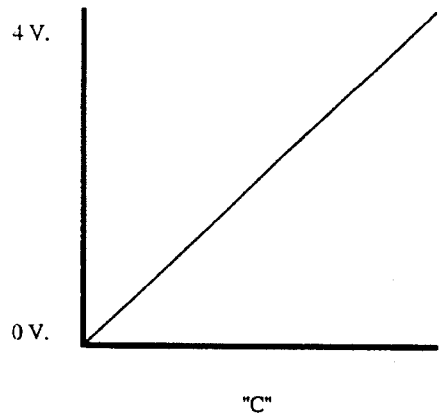
Figure 5D:
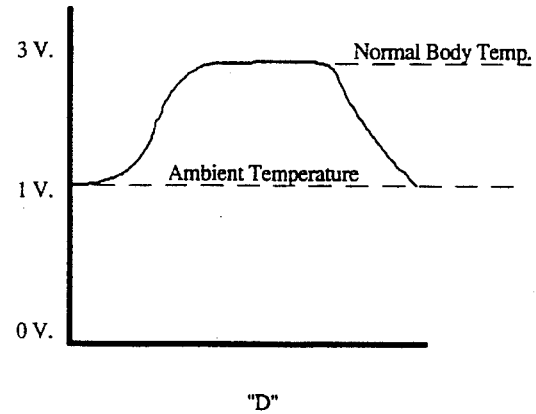
Figure 5E:
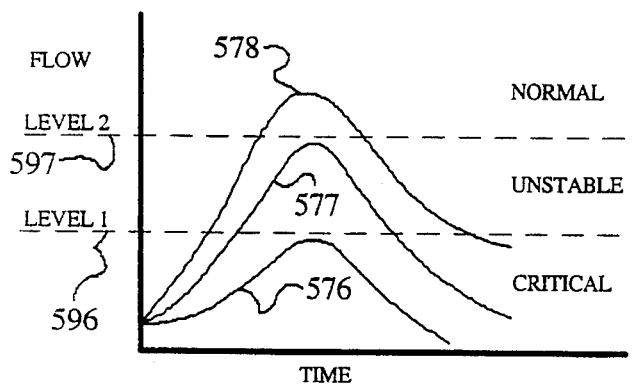

The first off-setting amplifier 555 has a gain of, for example 5, and the signal it generates is shown as wave form "B" in FIG. 5b. The second off-setting amplifier 560 has a gain of 20, for example. The wave form "C" shows the signal which is the output of the second off-setting amplifier 560. In operation of the circuitry thus far, the signal presented to the input of the first off-setting amplifier (waveform "A") is off set to zero volts and amplified. Wave form "A" of FIG. 5b shows the results of the effects of sensing element 430 as the user exhales into the apparatus. Note the signal starts from a stable state of 1 volt (which is the output of the servo loop in a quiescent state discussed earlier), and rises to 1.8 volts in the example (a difference of 0.8 volts). The microprocessor 570 analyzing the signal "A" via A/D converter 575 and commands the D/A converters 580 to output the first off set presented to the control input of amplifier 555. The wave form "B" is identical to wave form "A" except it rises and falls from zero to 4 volts, e.g., 5 times 0.8 volts equals 4.0 volts. The second off-setting amplifier 560 functions much the same except it has a gain of 20, and its task is to magnify the wave form of "B" still further. This is accomplished by segmenting the wave form "B" in time and voltage. In the example, the time and voltage indicated between the dotted lines of wave form "B" are amplified 20 times and shown in wave form "C", e.g., 2.0 volts minus 1.8 volts equals 0.2 volts times 20 equals 4.0 volts. This process in analyzing wave form "B" happens from 0.0 volts and zero time to maximum time. In each case, the second amplifier 560 is off set to zero via its control input as instructed by the microprocessor analyzing wave form "B" by means of the A/D converter and commanding the D/A converter second channel appropriately. In the preferred embodiment, the sample rate for analyzing the wave form "B" to produce wave form "C" is 200 time per second or once every 5 milliseconds.

A constant flow of current is available on common line 564 from a constant current source 505, and is being feed to pad 465 of the sensor array 240 through connector 325 and 315. This current flows through sensing element 462, to pad 435 system common. The resulting voltage across sensor 462 is sensed on line 564 into off-setting amplifier 565. This voltage is directly proportional to temperature of sensor 462. Off-setting amplifier 565 further amplifies and offsets this voltage at 465 which is connected to the A/D converter 575 of the microprocessor 570. The resulting temperature value is utilized to determine the proper flow direction (exhaling by user rather than inhaling) and correct the flow signal for temperature variations.

The wave form "D" is the signal representing the temperature sensing element 462 during a typical breath. All appropriate signals of wave forms "A", "B", "C" and "D" are temporarily stored in the clock and N.V. memory circuitry 585 until the peak expiratory flow rate (PEFR) and forced expiratory volume in 1st second (FEV1), is fully analyzed. After completion of the above process, the values PEFR and FEV1 are permanently stored in the non volatile memory.

The microprocessor 570 is further connected to the control/display 120 over bi-directional line 571. Information relating to the PEFR and FEV1 is displayed and is controlled via the push-buttons thereon. Also preprogrammed responses are indicated, to include audible alarms 595, as to the performance of the user and determined by the process above. Further discussion of results of the above process shall be disclosed in the operations section later.

Electronic switch 532 is connected to the feedback loop of operational amplifier 550 and bridge junction 525 on line 552. The output of switch 532 is connected through resister 533 to line 536. The control gate of electronic switch 532 is connected to the microprocessor 570 over line 534. When switch 532 is activated by the microprocessor, the switch and resistor 533 serve to raise the operating temperature of sensing element 430 by heating the wire sufficiently to self clean any contaminats on it such as mucus or phylum which the patient may cough-up in the process of using the apparatus 100. This "shorting" in effect of operational amplifier 550 causing the sensing element 430 to burn away debris, assures continuing relieable service of the peak flow measurements of the present invention and is cycled ON from time to time by predetermined instructions programed into the microprocessor.

A pressure transducer 590 is connected conventionally to system (+) potential and ground as indicated. The outputs of the pressure transducer 590 are connected to a differential amplifier 593 inputs over line 591 to the (+) input and over line 592 to the (−) input. The differential amplifier 593 output is connected to the microprocessor 570 A/D converter 575 over line 594. Signals of the circuits 590 and 593, are used for ambient air correction.

The communication connector 350 is connected to the microprocessor 570 over bi-directional line 573. When external cable is connected to communication connector 350, the system is powered externally to conserve battery life and shall be discussed in disclosure of FIG. 7.

It is important to understand that all components illustrated in schematic block diagram in FIG. 5a are representative of functional components and are commonly available in a diversity of configurations by many manufacturers. Such components are easily connected to one another by anyone skilled in the art as set forth in the diagram of FIG. 5a. It is to be expressly noted that while individual sensing elements 430 and 462 have a specific layout and pattern, as was set forth in FIG. 4 in the preferred embodiment, other layouts and patterns of sensing elements may be substituted to result in the same function.

Figure 6A:
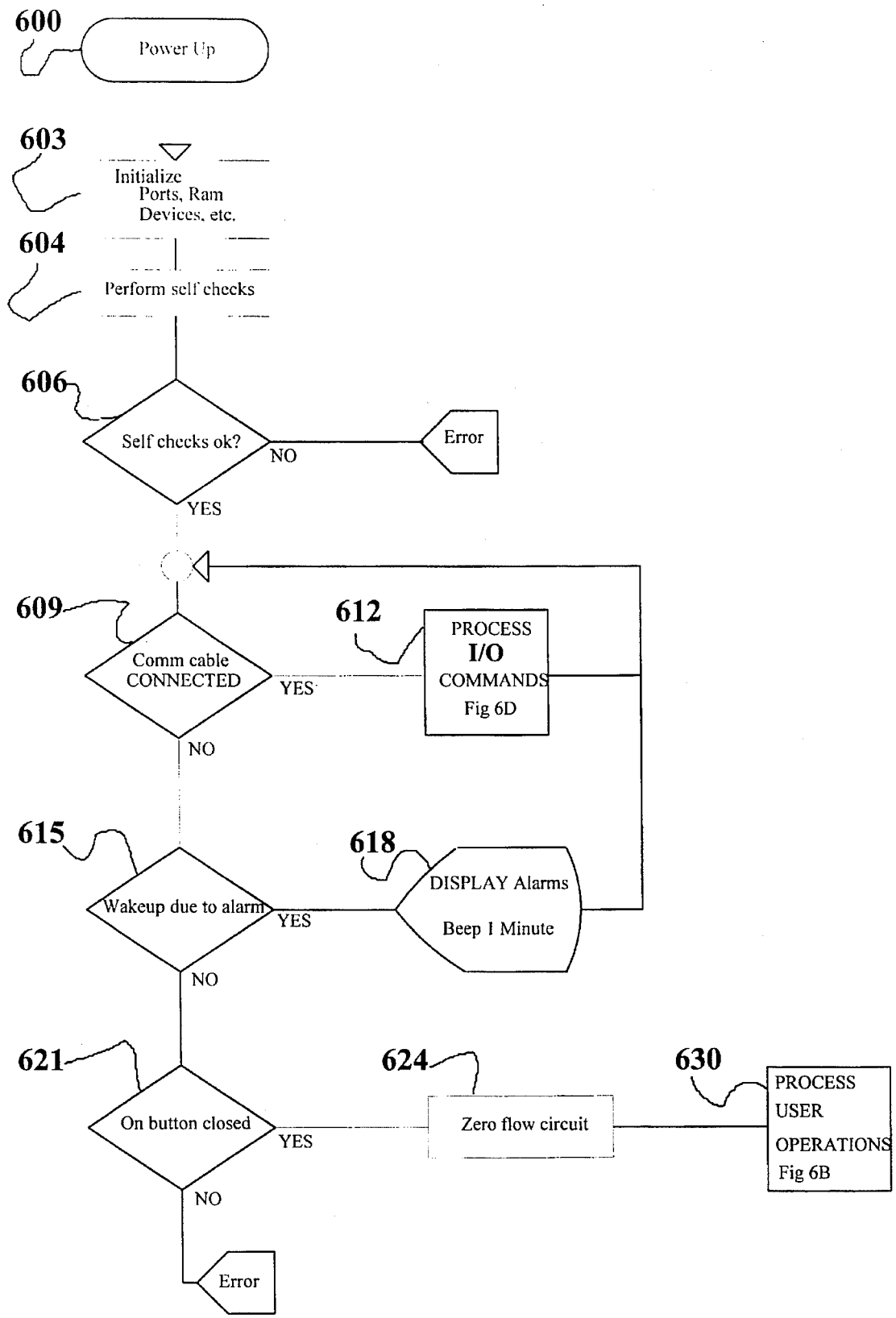
FIGS. 6A–6D set forth flow logic for the control circuit of FIG. 5.

FIGS. 6A through 6D set forth the logic of the device in the form of flow charts for the operation of the electronic circuitry (336). This process is driven according to instruction program code conventionally written according to the manufacturers data sheet recommendations for the desired result, as may be capable of the components, as anyone skilled in the art could perform. In FIG. 6A an overview of the device operation is given. An external event causes the device to enter state 600 which is the result of power being applied. Upon power up step 603 is entered within which initializes elements of the program and electronics, specifically program variables, microprocessor ports, RAM, clock chips and backup components.

Thereupon step 604 validates key elements of circuitry and program storage to determine if proper operation of the device is possible and if the cover 170 is in place. At step 606 the results of step 604 are evaluated and if the results are such that proper operation of the device is not possible the NO branch is taken which results in the device alarming and powering down. If operation is possible the program proceeds to step 609 which determines if the communications cable connector 705 is inserted into the device 350. If the cable is inserted program execution proceeds to step 612 to process Input/Output commands from the personnel computer (720) to be described later.

If the cable 705 is not inserted then execution proceeds to step 615 which evaluates if the cause of power being applied was because of a clock alarm from the result of preprogrammed schedule of usage downloaded previously. If the determination is such that an alarm caused the power up then an informative message is displayed to the user, such as "Time for Peak Flow" and the audio annunciator 595 is beeped until the user responds or 1 minute has elapsed. If the result of step 615 is such that an alarm was not the cause of power up then execution proceeds to step 621 where the ON button 215 is queried to determine if it is being depressed. If the result from step 615 is such that the ON button is not being pressed then it is considered to be an erroneous event and power is removed. If the result of step 615 is such that the button is being depressed then execution proceeds to step 624 where the electronics is directed to offset the zero flow values for later use. Execution then proceeds to process 630 which is detailed in FIG. 6B.

Continuing to step 632 a menu is presented on the display a single line at a time as described earlier utilizing the NEXT (225) and PREV (230) buttons to scroll through options and SELECT button 220 to select the appropriate item. All MENU items may not be available for any particular patient as they may be disabled by downloading options from the PC. This is not shown on FIG. 6B for simplicity. Individually the menu items are represented below step 632 as MANEUVER, DATA, ALARMS, CLOCK, and MAINTENANCE. Upon pressing the SELECT button 220 the current displayed item is determined and program execution proceeds to the appropriate next step individually 632A, 632B, 632C, 632D or 632E.

Step 634 executes a process detailed if FIG. 6C as performing a respiratory maneuver covered later. Step 636 allows the user to scroll through chronological data previously recorded such as PFER or FEV1 from respiratory maneuvers. Step 638 allows the patient to review his daily scheduled regimen of measurements to be performed. Step 640 allows the patient to check the current time and date. Step 642 is a submenu not detailed allowing the testing of the device and inspection of program settings. This option would normally be disallowed to the patient.

Figure 6B:
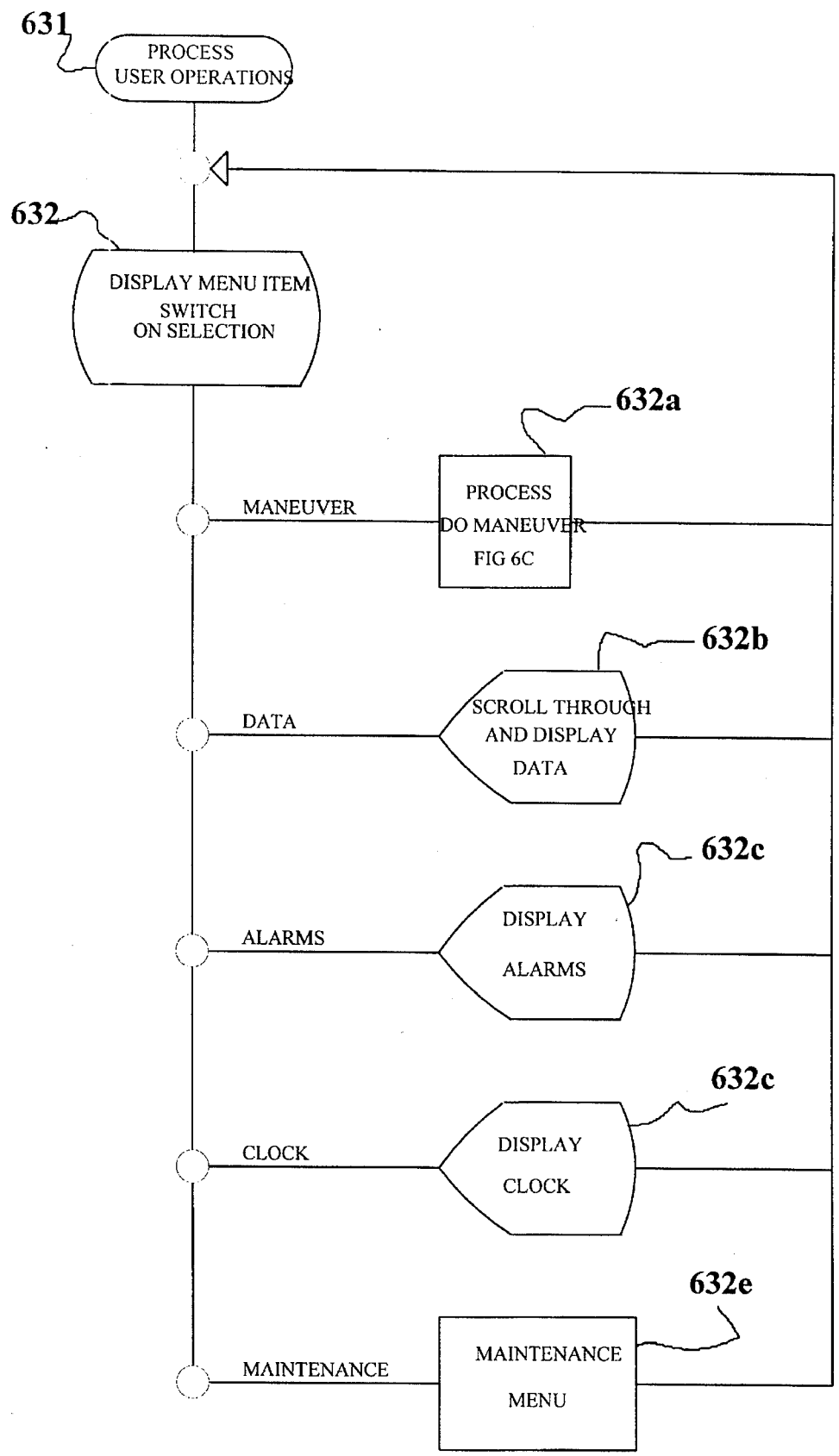
Figure 6C:
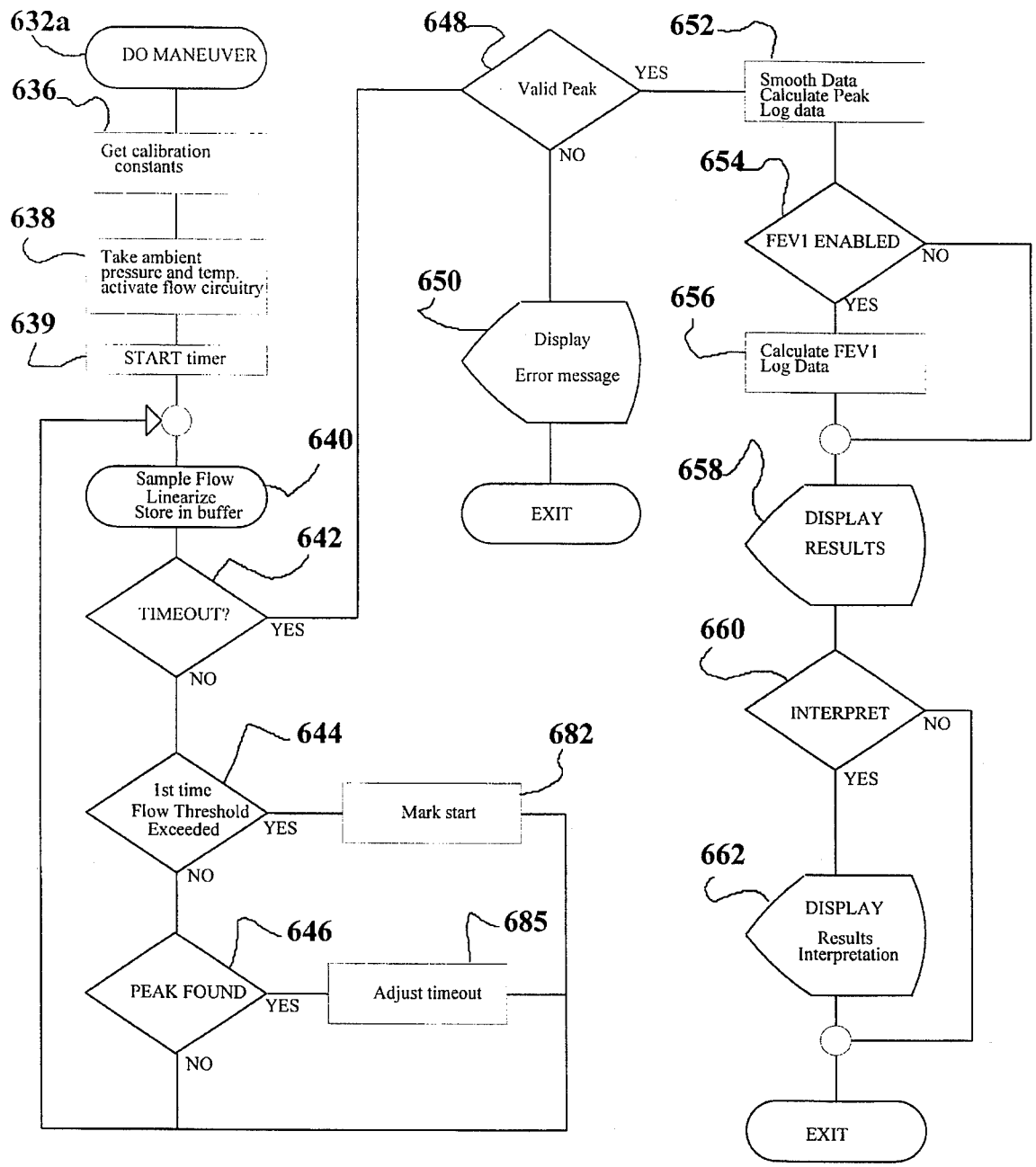

FIG. 6C details the selection of process 634 DO MANEUVER of FIG. 6B. Proceeding to step 636 which retrieves calibration constants from the serial EEPROMS 410 on the flow sensor board not detailed schematically which pertain to the flow sensor, and on board EEPROMS which contain constants for the electronics. Step 636 utilizes these constants to calibrate measurements of ambient pressure and ambient temperature from the sensors 590 and 462 respectively. These are utilized in the calibration equations for the flow sensor 430. Finally, step 638 activates the power to the flow sensor 430 to allow a measurement to begin. Step 639 initiates a timer which is utilized in the following step 642 for a measurement timeout. A flow sampling loop is initiated in step 640 and following. Step 640 samples the flow sensor as described previously about FIG. 5A linearizes the values and stores in a circular buffer. This process continues until at step 642 the timer has exceeded the measurement timeout set previously. If timeout has not occurred then at step 644 the flow is tested against a threshold to determine if onset of expiration has occurred at which time step 682 marks the spot in the buffer where this occurs for later steps to calculate the respiratory measurements. Step 646 checks the flow data buffer to determine if a valid peak has been found which if it has proceeding to step 685 modifies the timeout parameters to adjust for completing a respiratory maneuver.

Once a timeout has been detected at step 642 proceeding to step 648 validates whether during the measurement cycle a valid flow event was detected. If not proceeding to step 650 an error message is displayed and control return to the menu level of FIG. 6B. If so proceeding to step 652 the data in the flow buffer is smoothed with a digital filter algorithm, the PFER (peak flow) is calculated and logged into the data log memory. If the FEV1 measurement has been enabled step 654 proceeds to calculate FEV1 and additionally log it. If at step 654 FEV1 has not been enabled control proceeds to 658 which displays the selected results of PFER and FEV1. Step 660 determines from option settings whether the interpretation of results has been enabled. If not control proceeds to return to the main menu. If so then interpretation of the PFER and FEV1 proceeds according to the downloaded directions from the personal computer as predetermined by the physician. These interpretations may be simply varying thresholds where such feedback as NORMAL, UNSTABLE, CRITICAL CALL DOCTOR may be given to the patient through the display. For example, the predetermined levels 596 and 597 of FIG. 5b "E", show waveform 576 as being unacceptable expiratory flow within the "CRITICAL CALL DOCTOR" region. The waveform 577 indicates the expiratory flow is "UNSTABLE", while the waveform 578 falls within "NORMAL" region. The interpretations may be more complex algorithmic interpretations of daily variations of flow measurements.

Figure 6D:
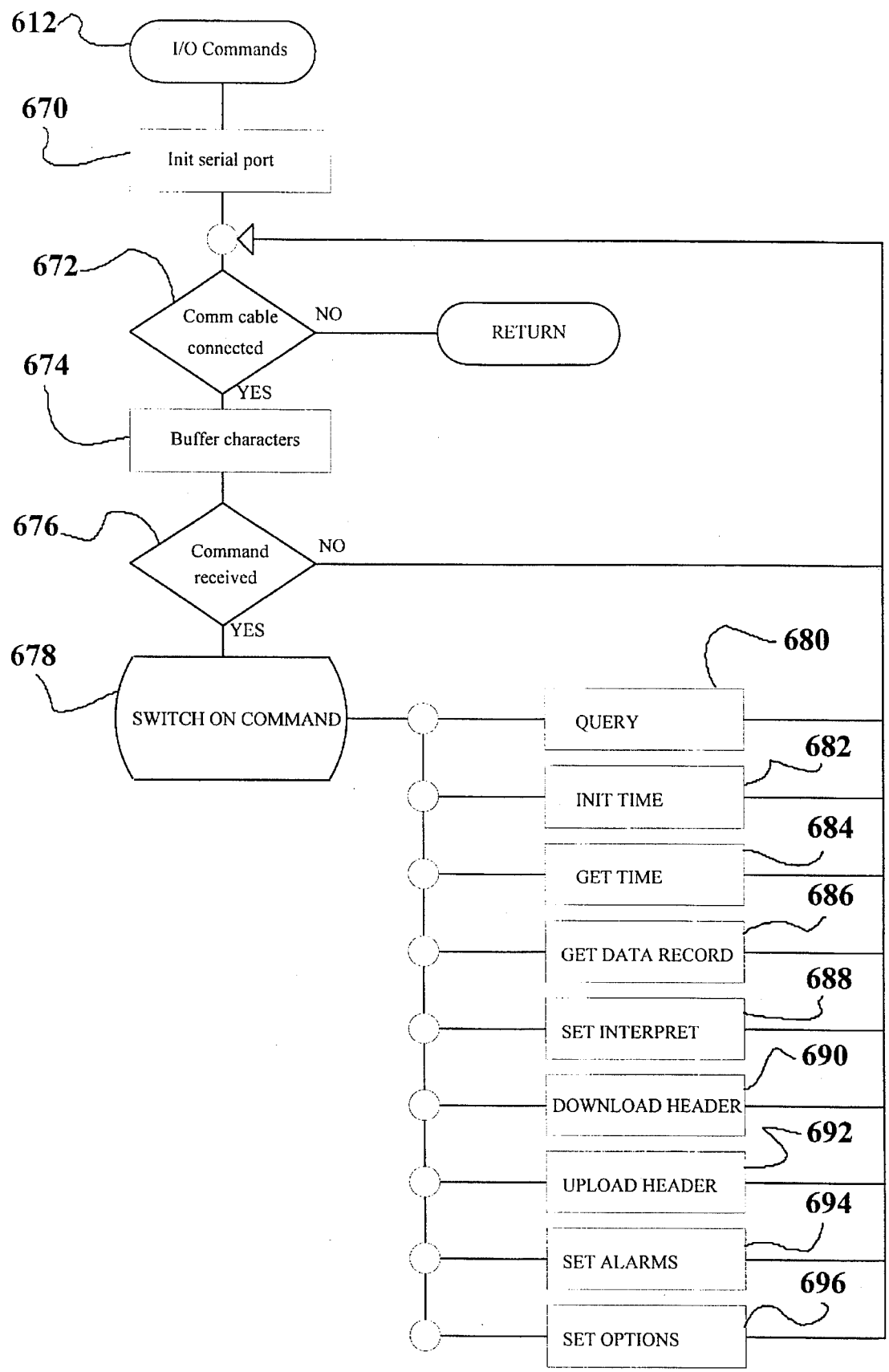

FIG. 6D details process 612 I/O commands entered from FIG. 6A. When the communications cable connector 705 is connected to device 350, process 612 begins at step 670 which firstly initializes the serial communications port in the microprocessor 570. Step 672 reexamines the presence of the communications cable such that when it is disconnected control passes back to FIG. 6A. Still connected execution proceeds to step 674 which is an interrupt driven loop buffering characters as they are received from the personal computer (PC 720 of FIG. 7). A command is received upon the receipt of an ASCII carriage return character. This is 720 of FIG. 7 determined in step 676 which continues to loop through steps 672 and 674 until receipt of this character, at which time execution proceeds to step 678 which is a command dispatcher switching on the contents of the command buffer to one of the individual steps 680 through 696.

Beginning with step 680, which would be executed, following a QUERY command, a response of the internal status of the device such as battery voltage is returned to the PC. Step 682 INIT TIME initializes the internal clock of the device with information from the PC. Step 684 GET TIME retrieves the current clock settings in the device to the PC. Step 686 GET DATA RECORD retrieves a chronological data record from the data log memory of the device. Step 688 SET INTERPRETATION sets the internal algorithms and messages to give feedback to the patient after each measurement. Step 690 DOWNLOAD HEADER is used to download patient name and other information to identify the user of the device. Step 692 UPLOAD HEADER is utilized to retrieve the patient information. Step 694 SET ALARMS is utilized to program in the usage regimen desired by the physician which will provide alarms as previously described. Step 696 SET OPTIONS allows the physician to specify which measurements are to be performed and in what manner. For example whether FEV1 is to be displayed and logged in addition to PFER. Another example is whether full menus are enable for the patient to be able to display data and alarms etc.

IN OPERATION

The apparatus 100 before use by a patient would be programmed by the physician through a PC and the communications cable connector 705 as described previously setting the various options, time, patient information, usage regimen and alarms, and feedback interpretation settings. Once the apparatus 100 is issued to a patient for use as part of therapy for asthma or other respiratory disease the patient will be able to keep the device in their possession due to its miniature size and portability. According to the regimen programmed in the device an alarm will sound and be displayed requesting that the patient perform to the appropriate respiratory maneuver.

Upon responding to the alarm or another request to perform a maneuver the patient would press the ON key clearing the alarm and powering the device as previously described. During the power up sequence the patient would be instructed to remove the cover 170 after a flow sensor autozero cycle has been performed. A menu of options would be presented and in the simplest case the patient would select PERFORM A MANEUVER currently being displayed as menu item number one by pressing the select button. Whereupon the display would coach the patient with a message to INHALE FULLY AND BLOW MAXIMALLY or the equivalent. The microprocessor at this time is executing program steps 640 through 646 awaiting a proper expiratory signal as in wave form "E" of FIG. 5b.

Once a peak has been determined and sufficient time has elapsed to ensure a full breath the logic proceeds to validate the measurement as described earlier. If the peak was found to be good it is displayed on the display such that the patient may view it. Most likely the physician will have enabled patient feedback and thusly an interpretive message will be displayed depending on the value of PFER. For a value indicating good performance the message NORMAL might be displayed as indicated in wave form "E" of FIG. 5b. If FEV1 is enabled the patient may press button 225 NEXT to get the displayed readout of FEV1. If the option has been enabled from the physician the entire expiratory maneuver may be displayed on 210 for the patient or physician.

If the value for PFER was insufficient as determined by the downloaded interpretation from the physician, then different instructions may be give the patient such as DO ANOTHER MANEUVER and then following if values are still low to advise the patient to call for assistance or take their medication and try later. An additional alarm may be calculated based on this determination.

If enabled at power on, with the apparatus 100 the patient may review his performance history by looking at individual values in the data log. Additionally, the patient might view the time history in graphical form to see his trend which is a normal component in the therapy for Asthma. Currently this is done by manually graphing a daily diary. The invention automates the manual diary and the graphing of the same.

Upon the patient returning to the physicians office or through a modem connection to his office through the communications cable, the log of PFER and FEV1 values since issuance to the patient may be retrieved by the physician. The physician may then review the performance history of the patient and from this review may determine the effectiveness of the medication regimen or the compliance to therapy by the patient. Modifications to the medication or education of the patient may follow with reissuance of the invention.

Figure 7:
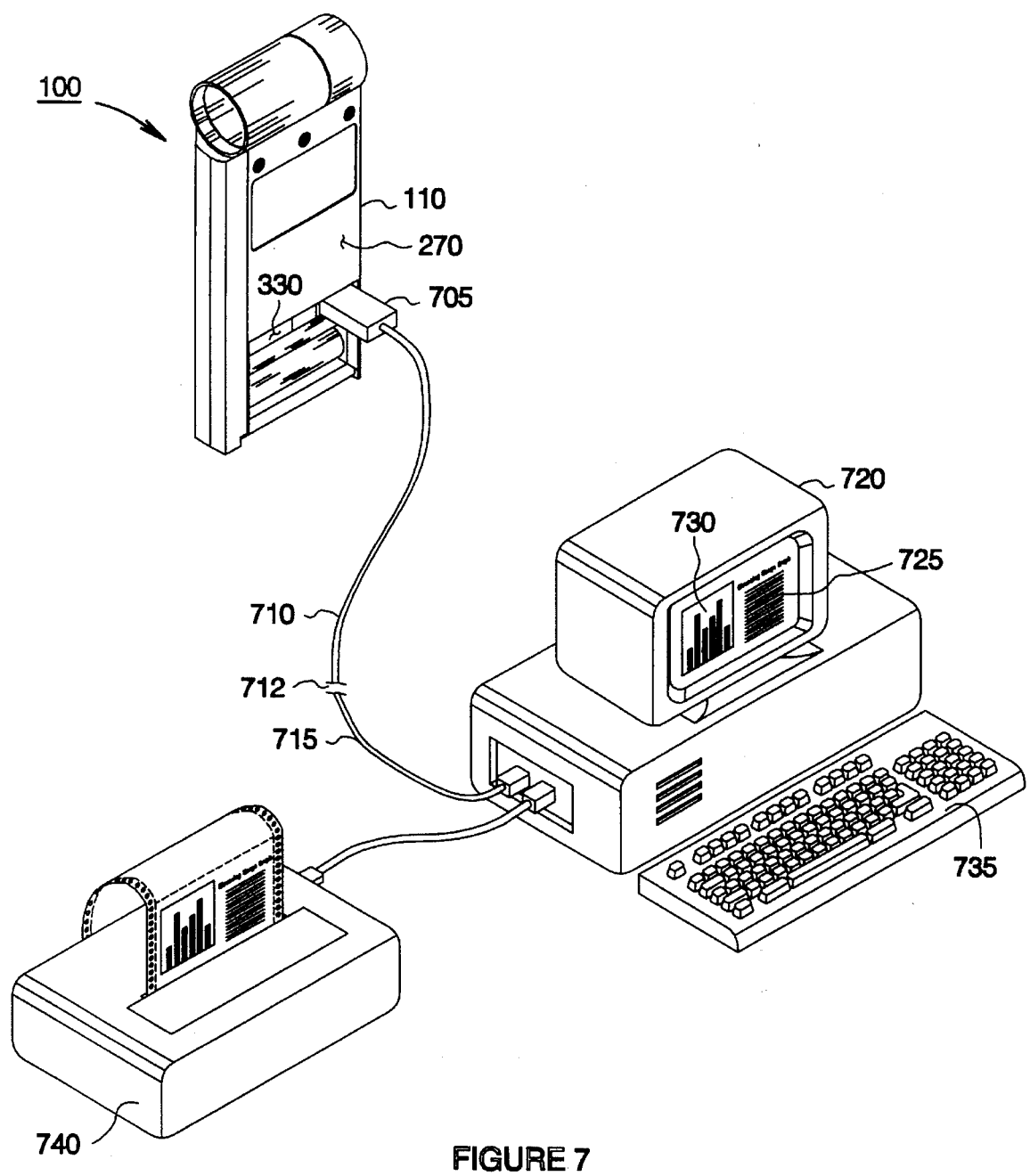
FIG. 7 sets forth an illustration of the system of the present invention being connected to a data retrieval device.

In FIG. 7 the electronic chronolog apparatus 100 has its battery access panel 270 removed and exposing communication connector receptacle 350. External communications cable connector 705 is connected to matted receptacle 350 mounted on the electronics assembly 330 as identified in FIG. 3. Communications cable 710 and 715 attach to computer 720. The junction 712 illustrates that communication modems may be in the data path transmission over cables 710 and 715 for remote retrieval of chronolog stored records. Computer 720 accesses the data base in the chronolog apparatus 100 for retrieval and analysis of the expiratory performance of the patient is displayed in tabulated statistical form 725 and graphically as in 730. Such information may be stored in computer memory for combining with other similar chronolog users data and further printed to hard copy utilizing printer 740. Keyboard 735 is manipulated in conventional manner to program apparatus 100 for scheduling if required by doctor. Retrieved information 725 and 730 also could represent a diagnostic report of the apparatus 100 over the full recorded period of time which includes battery and sensor response. This information, under analysis, indicates if the instrument was functioning properly. The computer, printer, cabling and connectors are all conventional and well known and are easily operable by anyone skilled in data handling.

The emphasis here is that positive reporting of expiratory behavior and performance is diligently recorded and analyzed to assure the benefits of the medicine doing what the doctor prescribes based on reliable feedback information.

While the invention has been particularly described and illustrated in detail with reference to the preferred embodiments and modifications thereof, it should be understood by those skilled in the art that equivalent changes in form and detail may be made without departing from the true spirit and scope of the invention as claimed, except as precluded by the prior art. The embodiments of the invention for which an exclusive privilege and property right is claimed are defined as follows:

What is claimed is:

1. A portable spirometric device for analyzing the flow rate and volume of exhalation of a patient under a doctor's care, the device recording, storing and displaying respiratory movement of the patient, the device comprising:

electronic package means mounted inside a hand held housing for computing and recording the flow rate and volume of the exhalation;

an air flow chamber mounted on said housing with a mouthpiece attached to and communicating with said air flow chamber;

a hot wire acting as an anemometer for sensing exhaled air flow rate through said mouthpiece, said hot wire mounted inside said air flow chamber, said air flow chamber removably attached to said housing and including a memory chip connected to said electronic package means and said hot wire, said memory chip programmed with calibration and operating information for said hot wire; and a signal generating means for determining the air flow rate through said mouthpiece, said signal generating means connected to said hot wire and to said electronics package means.

2. The device as described in claim 1 wherein a first portion of said hot wire is used for sensing air flow rate and a second portion of said hot wire is used for sensing air flow temperature.

3. The device as described in claim 1 wherein said hot wire is mounted so as to be in a plane parallel to the exhaled air flow in said air flow chamber for reducing size and air flow resistance therein.

4. The device as described in claim 1 further comprising a display means on said housing connected to said electronic package means for displaying air flow data characterizing the patients respiratory performance.

5. The device as described in claim 4 wherein said electronic package means is pre-programmed by the doctor with interpretive feedback and recommendations as to necessary medication based on the measured air flow rate through said mouthpiece and displayed on said display means.

6. The device as described in claim 1 wherein said mouthpiece is disposable and removably attached to said air flow chamber.

7. A portable spirometric device for analyzing the flow rate and volume of exhalation of a patient under a doctor's care, the device recording, storing and displaying respiratory movement of the patient, the device comprising:

electronic package means mounted inside a hand held housing for computing and recording the flow rate and volume of each exhalation, a display means on said housing connected to said electronic package means for displaying air flow rate of each exhalation, said electronic package means programmed to sound an alarm and provide a display on said display means for requesting the patient perform an appropriate respiratory maneuver based on measured exhaled air flow rate and air flow temperature;

a removable air flow chamber mounted on said housing with a disposable mouthpiece releasably attached to and communicating with said air flow chamber;

a hot wire acting as an anemometer for sensing exhaled air flow rate and volume through said mouthpiece, said hot wire mounted inside said air flow chamber; and a signal generating means for determining the air flow rate and volume through said mouthpiece, said signal generating means connected to said hot wire and to said electronic package means.

8. The device as described in claim 7 wherein a first portion of said hot wire is used for sensing air flow rate and a second portion of said hot wire is used for sensing air flow temperature, the first portion of said hot wire operating at a greater temperature than the second portion of said hot wire.

9. The device as described in claim 8 wherein the first portion of said hot wire operates at a temperature great enough for burning off any contaminates introduced by exhaled air through said air flow chamber.

10. The device as described in claim 7 wherein said mouthpiece includes a fine mesh screen used as an aid in removing contaminates by exhaled air through said air flow chamber and protecting said hot wire.

11. The device as described in claim 7 further including a remote retrieval and data processing means electrically connected to said electronic package means for retrieval of stored data for analysis by the doctor.

12. The device as described in claim 7 wherein said electronic package means is preprogrammed by the doctor and including time, date, patient information, usage regimen and alarms, and feedback interpretations settings.

13. The device as described in claim 7 wherein said device further includes an air flow chamber and mouthpiece cover means for preventing air flow therethrough prior to its removal, said cover means allowing said electronic package means to perform a "zero" air flow calibration prior to removing said cover by the patient.

14. The device as described in claim 7 wherein said air flow chamber includes an open first end for receiving said mouthpiece and an open second end, the exhaled air flow passing through said air flow chamber from the open first end, past said hot wire and exiting out the open second end without passing into or through said housing.

15. A portable spirometric device for analyzing the flow rate and volume of exhalation of a patient under a doctor's care, the device recording, storing and displaying respiratory movement of the patient, the device comprising:

electronic package means mounted inside a hand held housing for computing and recording the flow rate and volume of each exhalation;

a removable air flow chamber mounted on said housing with a disposable mouthpiece releasably attached to and communicating with said air flow chamber, said air flow chamber including an open first end for receiving said mouthpiece and an open second end;

a hot wire acting as an anemometer for sensing exhaled air flow rate and volume through said mouthpiece, said hot wire mounted inside said air flow chamber, a first portion of said hot wire is used for sensing air flow rate and a second portion of said hot wire is used for sensing air flow temperature, the first portion of said hot wire operating at a temperature great enough for burning off any contaminates introduced by exhaled air through said air flow chamber, the exhaled air flow passing through said air flow chamber from the open first end, past said hot wire and exiting out the open second end without passing into or through said housing; and a signal generating means for determining the air flow rate and air flow volume through said mouthpiece, said signal generating means connected to said hot wire and to said electronic package means.

16. The device as described in claim 15 further including a remote retrieval and data processing means electrically connected to said electronic package means for retrieval of stored data for analysis by the doctor.

17. The device as described in claim 15 further comprising a display means on said housing connected to said electronic package means for displaying the air flow rate of each exhalation, said electronic package means programmed to sound an alarm and provide a display on said display means for requesting the patient perform an appropriate respiratory maneuver based on measured exhaled air flow rate and air flow temperature.

* * * * *